US00PP27075P3

(12) United States Plant Patent
Klemm et al.

(10) Patent No.: US PP27,075 P3
(45) Date of Patent: Aug. 16, 2016

(54) *CALIBRACHOA* PLANT NAMED 'KLECA14265'

(50) Latin Name: ***Calibrachoa* sp.**
Varietal Denomination: KLECA14265

(71) Applicant: Klemm+Sohn GmbH & Co. KG, Stuttgart (DE)

(72) Inventors: Nils Klemm, Stuttgart (DE); Anita Stöver, Ostfildern (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 107 days.

(21) Appl. No.: 14/544,270

(22) Filed: Dec. 15, 2014

(65) Prior Publication Data
US 2016/0174447 P1 Jun. 16, 2016

(51) Int. Cl.
*A01H 5/02* (2006.01)

(52) U.S. Cl.
USPC ..... Plt./413

(58) Field of Classification Search
USPC ..... Plt./413
See application file for complete search history.

*Primary Examiner* — Anne Grunberg
(74) *Attorney, Agent, or Firm* — Barbara Campbell; James M. Weatherly; Cochran Freund & Young, LLC

(57) ABSTRACT

A new *Calibrachoa* plant particularly distinguished by having red-purple flowers and a semi-upright habit plant form and habit, is disclosed.

1 Drawing Sheet

Genus and species: *Calibrachoa* sp.
Variety denomination: 'KLECA14265'.

BACKGROUND OF THE NEW PLANT

The present invention comprises a new and distinct variety of *Calibrachoa*, botanically known as *Calibrachoa* sp., and hereinafter referred to by the variety name 'KLECA14265'. 'KLECA14265' originated from a controlled cross conducted in May 2010 in Stuttgart, Germany between the proprietary female *Calibrachoa* variety 'CA-2009-1319' (unpatented) and the proprietary male *Calibrachoa* variety 'KLECA09172' (U.S. Plant Pat. No. 22,152).

In May 2010, seed was collected from the controlled cross between the two *Calibrachoa* parental lines. The seeds were sown and plants were grown for evaluation in Stuttgart, Germany. A single plant line was selected in May 2011 which had red-purple flowers and was subsequently named 'KLECA14265'. In May 2011, 'KLECA14265' was first vegetatively propagated by tip cuttings. 'KLECA14265' was found to reproduce true to type in successive generations of asexual propagation via tip cuttings.

SUMMARY

The following are the most outstanding and distinguishing characteristics of this new variety when grown under normal horticultural practices in Stuttgart, Germany.

1. Red-purple flowers; and
2. A semi-upright form and habit.

DESCRIPTION OF THE PHOTOGRAPH

This new *Calibrachoa* plant is illustrated by the accompanying photograph which shows the whole plant, including the habit, the foliage, the flowers, and the buds, and a close-up of the flowers. The photograph is of a four-month-old plant grown in a pot outdoors in Stuttgart, Germany in July 2013.

The colors shown are as true as can be reasonably obtained by conventional photographic procedures.

DESCRIPTION OF THE NEW VARIETY

The following detailed descriptions set forth the distinctive characteristics of 'KLECA14265'. The data which define these characteristics were collected from asexual reproductions carried out in Stuttgart, Germany. Data was collected on 11-week-old plants grown in a controlled glass greenhouse environment in Stuttgart, Germany in May 2013. Color references are to The R.H.S. Colour Chart of The Royal Horticultural Society of London (R.H.S.) (2007).

Classification:
- *Family.*—Solanaceae.
- *Botanical.*—*Calibrachoa* sp.
- *Common.*—*Calibrachoa.*
- *Designation.*—'KLECA14265'.

Parentage:
- *Female parent.*—Proprietary *Calibrachoa* line 'CA-2009-1319' (unpatented).
- *Male parent.*—*Calibrachoa* line 'KLECA09172' (U.S. Plant Pat. No. 22,152).

Plant:
- *Life cycle.*—Annual.
- *Form and habit.*—Semi-upright.
- *Height (from soil line to top of foliage).*—7.0 cm.
- *Spread.*—16.0 cm.
- *Propagation.*—Vegetatively propagated by tip cuttings.
- *Time to produce a rooted cutting.*—3 weeks.

Stems:
- *Stem color.*—RHS 145A.
- *Pubescence.*—Absent.
- *Diameter.*—0.1 cm.
- *Length, from soil line to first node.*—1.4 cm.
- *Total length.*—8.0 cm.
- *Internode length.*—2.5 cm.

Leaves:
*Arrangement.*—Alternate, simple, and sessile.
*Shape.*—Elliptic.
*Apex.*—Obtuse to slightly acute.
*Base.*—Attentuate.
*Margin.*—Entire.
*Surface.*—Smooth.
*Surface pubescence.*—Absent.
*Venation.*—Pinnate.
*Venation color.*—Upper surface: RHS 144A. Lower surface: RHS 145B.
*Length.*—3.0 cm.
*Width.*—0.6 cm.
*Color.*—Upper surface: RHS 141A. Lower surface: RHS 141D.
*Fragrance.*—Absent.

Flowers:
*Flower type and habit.*—Single flowers having determinate inflorescence.
*Flowering requirements.*—A minimum of light sun is required.
*Duration of flowers.*—6 days.
*Corolla texture.*—Smooth texture.
*Corolla shape.*—Trumpet-shaped.
*Fragrance.*—Absent.

Flower buds:
*Surface texture.*—Smooth.
*Length.*—2.2 cm.
*Diameter.*—0.5 cm.
*Shape.*—Irregular to oblong.
*Color.*—RHS 77A.

Peduncle:
*Length.*—2.5 cm.
*Diameter.*—0.1 cm.
*Color.*—RHS 146D.
*Texture.*—Smooth.
*Anthocyanin color.*—Absent.

Flower description:
*Flower depth.*—3.0 cm.
*Flower tube length.*—2.0 cm.
*Flower tube diameter.*—0.7 cm.
*Flower diameter.*—3.0 cm.
*Pedicel color.*—RHS 146D.
*Calyx.*—Funnel-shaped.

Sepals:
*Shape.*—Lanceolate.
*Apex.*—Acute.
*Margin.*—Entire.
*Length.*—1.5 cm.
*Diameter.*—0.2 cm.
*Sepal color.*—Upper surface: RHS 143A. Lower surface: RHS 143B.

Petals:
*Shape.*—Heart-shaped.
*Length.*—1.3 cm.
*Apex.*—Obverse.
*Margin.*—Entire, weak undulation.
*Base.*—Open and fused into the tube.
*Pubescence.*—Absent.
*Lobe length.*—1.2 cm.
*Lobe width.*—1.5 cm.
*Lobe color.*—Upper surface: RHS N74A. Lower surface: RHS 186B.
*Corolla tube color.*—Inner: RHS 7A. Outer: RHS 7D.
*Fragrance.*—Absent.

Reproductive organs:
*Stamen number.*—5.
*Stamen color.*—Anther color: RHS 13A. Filament color: RHS 2C. Pollen color: RHS 13A.
*Ovary.*—Placenta arrangement: Ovate. Pistil number: 1. Pistil length: 0.1 cm. Stigma color: RHS 144B. Style length: 1.0 cm. Style color: RHS 144D.

Fruit and seed set: Little seed production.
Disease and pest/insect resistance: None observed.

COMPARISON WITH PARENTAL LINES AND KNOWN VARIETY

'KLECA14265' is distinguished from the female and male parental lines as described in Table 1.

TABLE 1

Comparison with Parental Lines

| Trait | 'KLECA14265' | Female parent 'CA-2009-1319' | Male Parent 'KLECA09172' |
|---|---|---|---|
| Flower color | RHS N74A | RHS 65D and RHS N66D | RHS 46C |

'KLECA14265' is most similar to the *Calibrachoa* plant named 'KLECA13251' (U.S. application Ser. No. 14/121,076) and also commercially known as MINIFAMOUS 'Neo Pink'. Differences between the two varieties are described in Table 2.

TABLE 2

Comparison with Similar Variety

| Trait | 'KLECA14265' | 'KLECA13251' |
|---|---|---|
| Flower color | RHS N74A | RHS 73A |

We claim:

1. A new and distinct variety of *Calibrachoa* plant named 'KLECA14265' as illustrated and described herein.

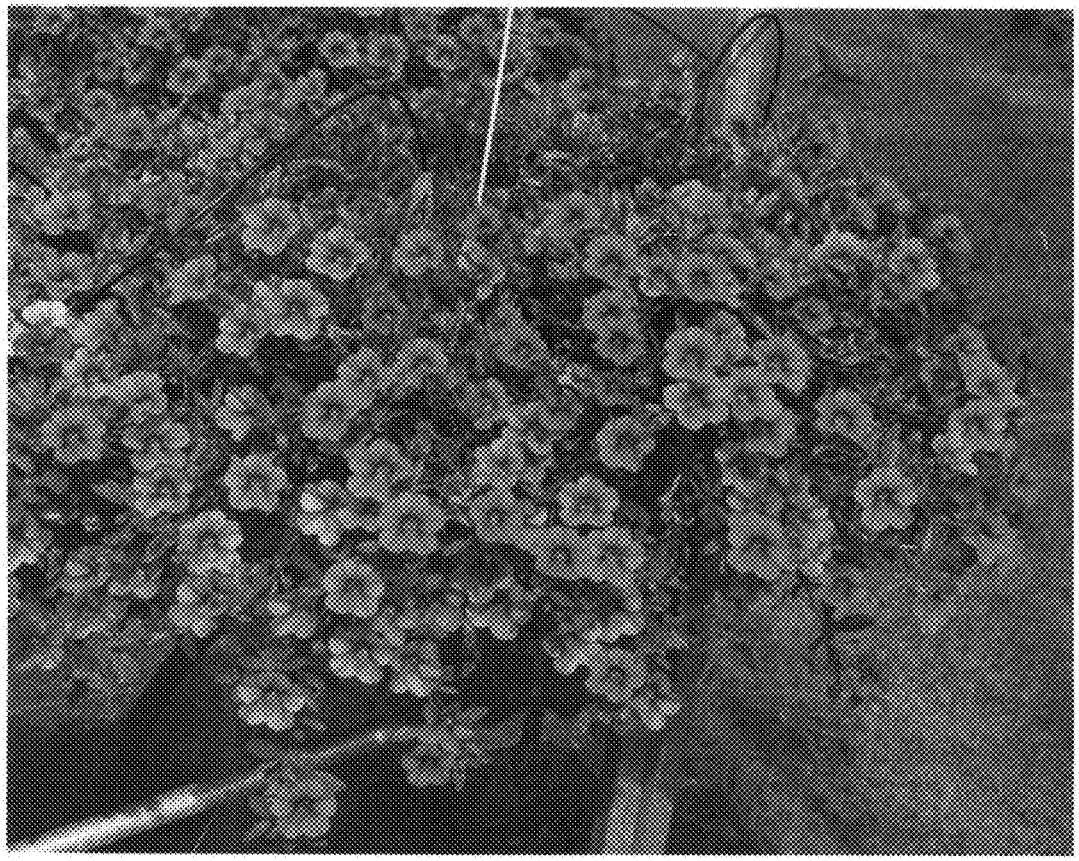

* * * * *